United States Patent [19]
Danley et al.

[11] Patent Number: 5,842,788
[45] Date of Patent: Dec. 1, 1998

[54] DIFFERENTIAL SCANNING CALORIMETER

[75] Inventors: Robert L. Danley, Collingswood, N.J.; John R. Reader, Jr., Newark; John W. Schaefer, Wilmington, both of Del.

[73] Assignee: TA Instruments, Inc., New Castle, Del.

[21] Appl. No.: 962,378

[22] Filed: Oct. 31, 1997

[51] Int. Cl.$^6$ .................................................. G01N 25/20
[52] U.S. Cl. ............................................. 374/12; 374/10
[58] Field of Search ................................... 374/10, 11, 12, 374/29, 30

[56] References Cited

U.S. PATENT DOCUMENTS

| | | | |
|---|---|---|---|
| 4,102,199 | 7/1978 | Tsipouras | 374/167 |
| 4,255,961 | 3/1981 | Biltonem et al. | 374/11 |
| 4,350,446 | 9/1982 | Johnson | 374/13 |
| 4,590,669 | 5/1986 | Imamura | 374/208 |
| 4,783,174 | 11/1988 | Gmelin et al. | 374/11 |
| 4,812,051 | 3/1989 | Paulik et al. | 374/10 |
| 4,848,921 | 7/1989 | Kunze | 374/11 |
| 4,971,452 | 11/1990 | Finney | 374/208 |
| 5,013,159 | 5/1991 | Nakamura et al. | 374/12 |
| 5,211,477 | 5/1993 | Li | 374/10 |
| 5,224,775 | 7/1993 | Reading et al. | 374/11 |
| 5,599,104 | 2/1997 | Nakamura et al. | 374/12 |
| 5,672,289 | 9/1997 | O'Neill | 374/11 |

*Primary Examiner*—Diego F.F. Gutierrez
*Attorney, Agent, or Firm*—Crowell & Moring LLP

[57] ABSTRACT

A Differential Scanning Calorimeter (DSC) which has constant calorimetric sensitivity over its entire range of operating temperatures from −200° C. to 540° C. The DSC sensor consists of a pair of thin-film Resistance Temperature Detectors (RTDs) which are used to sense the temperature of a sample and the temperature difference between the sample and an inert reference. The RTDs are supplied with an excitation current which varies according to the temperature of the reference to achieve constant calorimetric sensitivity, independent of the operating temperature.

26 Claims, 4 Drawing Sheets

DIFFERENTIAL SCANNING CALORIMETER

The present application claims priority based upon U.S. Provisional patent application Ser. No. 60/032,051, filed Nov. 1, 1996.

BACKGROUND

1. Field of the Invention

The present invention relates to heat flux different scanning calorimeters, and to the temperature sensors used in such calorimeters.

2. Background of the Invention

Heat flux differential scanning calorimeters (DSCs) are described in U.S. Pat. No. 5,224,775, which is incorporated herein by reference. Heat flux DSCs measure temperature differences within the DSC, which are proportional to the flow of heat to the sample. The temperature differences are measured using sensors at the sample position and at the reference position. The temperature differences are calibrated, such that the heat flow to the sample can be measured, as the sample and reference materials are subjected to dynamically controlled changes of temperature. Plots of the sample heat flow as a function of temperature provides information concerning physical transformations occurring in the sample material.

The sensor assembly in heat flux DSCs include temperature sensors mounted on a support structure which is mounted in an oven, which is a source or a sink for heat flowing into (or out of) the sensor assembly. The sample temperature sensor and the reference temperature sensor are attached to the sample and reference positions of the support structure. The sample temperature sensor measures a temperature representative of the temperature of the sample, and the temperature difference signal is obtained by measuring the difference between the sample and reference temperature signals. The sample temperature sensor is calibrated so that it closely matches the actual sample temperature, and the differential temperature sensor is calibrated to provide an accurate measure of the heat flow to (and from) the sample.

The measured temperature difference is created by the flow of heat between the oven and the sample and reference via the support structure. Thus, the measured temperature difference between the sample position and the reference position is dependent upon the geometry of the supporting structure, and on the thermal diffusivity of the material from which the supporting structure is constructed.

In principle, any of type of temperature sensor or differential temperature sensor may be used in a DSC. The most common types of temperature sensors used in heat flux DSCs are thermocouples, thermopiles and resistance temperature detectors (RTDs). Thermocouples and thermopiles generate a voltage which depends upon the temperature of the junction. Using calibration tables, the temperature of the junction between thermoelectrically different materials can be determined from a measurement of the voltage. However, the voltage generally becomes progressively smaller as temperature decreases, which reduces the sensitivity of thermocouple temperature sensors at lower temperatures.

Because the electrical resistance of a conductor depends on the temperature of the conductor, RTDs measure temperature by measuring the resistance of a conductor, and using appropriate calibration procedures and tables to compute the temperature of the conductor from its resistance. The most widely used type of RTDs are platinum RTDs. For platinum RTDs, the resistance of the platinum decreases with decreasing temperature. If a known electrical current is passed through the platinum RTD, the resultant voltage which appears across the terminals of the RTD is a measure of the temperature of the RTD. The output voltage of the RTD is directly proportional to the applied current, so increasing the current increases the RTD signal, making high currents desirable.

Because of the variation of the voltage output of the temperature sensor as a function of temperature, and the variation of thermal diffusivity of the supporting structure as a function of temperature, the voltage output of a conventional DSC sensor varies considerably with temperature. Typically, the voltage output of a differential thermal analysis sensor falls rapidly below ambient temperature. Furthermore, because transitions which occur at low temperatures are generally quite weak, detection of low temperature transitions is particularly difficult as temperatures decrease.

The dynamic response of a sensor for a DSC is a parameter that describes how rapidly the sensor reacts to a change in heat flow. Sensors with rapid dynamic responses are desirable for three reasons. First, if the sensor has a slow response, the measured temperature will lag the actual temperature. Second, if two transitions occur at temperatures which are in close proximity to each other, the overlap of the two transitions will be greater if the sensor has slow response. Third, in the Modulated DSC® technique (MDSC®), which is described in U.S. Pat. No. 5,224,775, the sample temperature is driven by the combination of a linear temperature ramp and a superimposed periodic temperature variation. When sensors with slow dynamic responses are used to perform MDSC measurements, the choices of the ramp rate and the period of the temperature modulation can be limited by the slow dynamic response of the sensor.

In conventional DSCs, calorimetric sensitivity and dynamic response have an inverse dependence: increasing the calorimetric sensitivity decreases the dynamic response, and vice versa. This is because rapid dynamic response is obtained by increasing the rate at which heat can be transferred between the oven and the sample and reference. The rate of heat transfer between the oven and the sample and reference is dependent upon the thermal resistance of the support structure: decreasing thermal resistance of the support structure increases the rate of heat transfer to and from signal and reference, and decreases the measured temperature difference between sample and reference and hence the measured signal for a given heat flow.

The flow of an electric current through a conductor generates heat equal to the product of the resistance of the conductor and the square of the current. Heat generated within the resistance element of an RTD by this mechanism causes temperature measurement errors because the heat generated increases the temperature of the element resulting in a high temperature measurement. This is known as "self-heating error". The magnitude of the resultant error depends upon how much heat is generated and how well the heat can be dissipated, which in turn depends upon how the RTD is constructed and mounted. Because of the uncertainty introduced by these factors, the conventional approach has been to keep RTD currents as low as possible while maintaining a sufficiently high RTD output.

RTD sensors generally fall into two categories, wirewound RTDs and thin film RTDs. Wire-wound RTDs use a fine platinum wire wound on an electrically insulating support as the resistor. The resistor is inserted in an electrically insulating tubular enclosure. The platinum wire has limited thermal contact with the support and, in turn, with the enclosure. Therefore, heat generated in the wire is not easily dissipated to the surroundings of the RTD. Therefore, self-heating errors can become quite large unless the RTD current is kept very low. In addition, the RTD enclosure may have limited ability to dissipate heat to its surroundings. For example, if the RTD is immersed in stagnant gas, heat dissipation will be limited. This limited ability to dissipate heat to the surroundings of the RTD further restricts the RTD current to low values.

Thin film RTDs comprise a thin film of platinum deposited in a serpentine pattern on an electrically insulating substrate. The platinum resistor is covered with a dielectric, e.g., a glass or an alumina layer, to protect it from physical damage. Because the resistor exists as a thin film deposited directly on the substrate, the thermal resistance between the resistor and the enclosure is eliminated and the temperature of the resistor and its enclosure will be essentially identical. Thus, one source of self-heating errors is removed. The problem of dissipation of heat from the RTD enclosure to its surroundings is still present, however, and may result in self-heating errors.

SUMMARY OF THE INVENTION

The present invention is a differential scanning calorimeter that has constant calorimetric sensitivity. The present invention uses two RTD sensors whose current is varied as a function of temperature, such that the amplitude of the signal produced by the RTD is constant, for a given heat flow, over the entire range of the DSC's operating temperatures. The DSC sensor of the present invention comprises a pair of platinum thin-film resistors supported by an electrically insulating substrate. One of the thin-film platinum resistors measures the temperature of the sample region of the support, and the other thin-film resistor measures the temperature of the reference region of the support. The amplitude of the sensing current for each RTD is selected based upon the temperature of that RTD.

The voltage across the sample thin-film resistor is a measure of the temperature of the sample, and the difference between the voltages across the sample and reference thin-film resistors is a measure of the differential flow of heat to the sample. Because the thin film platinum resistors are an integral part of the support, and because the temperature of the support is the parameter that is actually being measured, there is no measuring error due to heat generation in the platinum resistors, and the sensing current can be freely chosen. Thus the current applied to the sensor can be varied, according to the temperature of the sensor, to offset the changes in calorimetric sensitivity due to changes in the resistance of the sensing element and changes in thermal diffusivity of the support means. A differential scanning calorimeter made in accordance with this invention will therefore have a calorimetric sensitivity which is constant over the range of operating temperatures.

Figure 1:
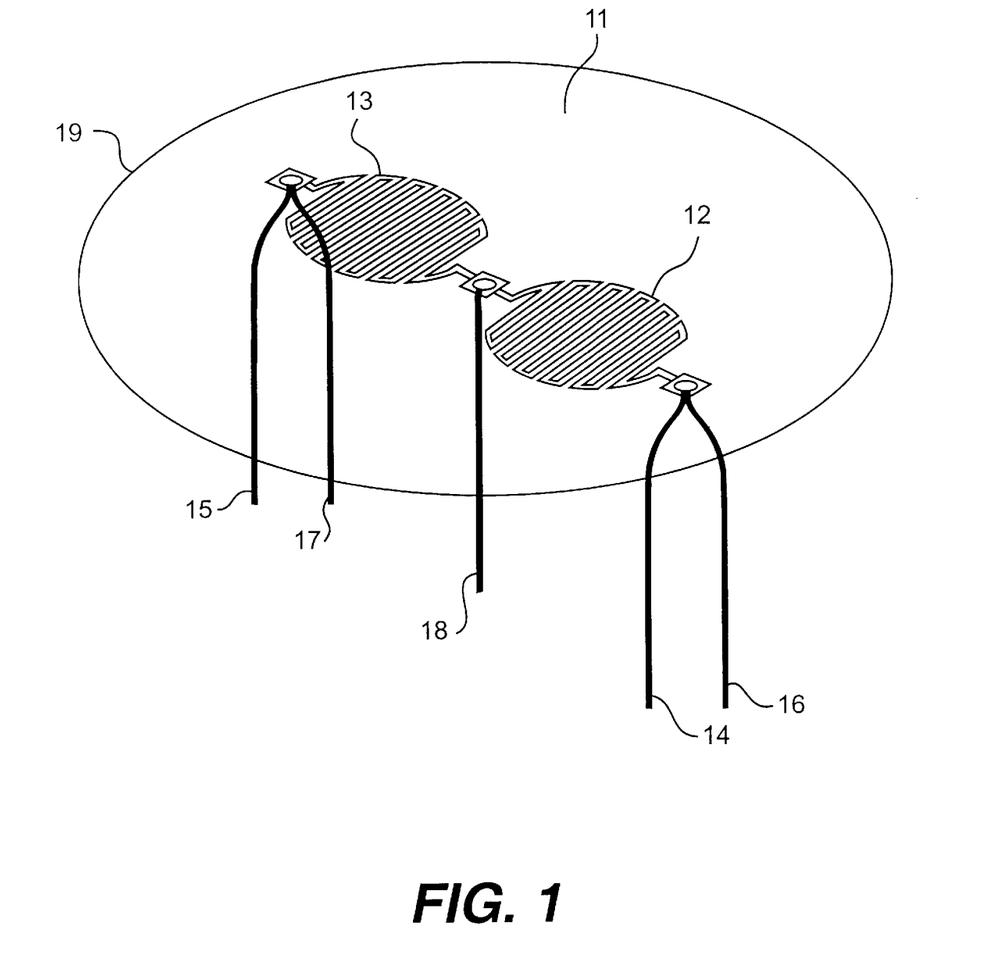
FIG. 1 is a schematic diagram showing the construction of a disk-type differential scanning calorimeter sensor using RTD temperature sensors for use in a constant calorimetric sensitivity differential scanning calorimeter system.

As shown in FIG. 1 and FIG. 1a, the thin-film RTD of the present invention is fabricated by depositing a serpentine thin film of platinum on an electrically insulating substrate. The thin platinum film is covered with a protective layer of a dielectric material, such as alumina or glass. Because the resistance element is an integral part of the substrate on which it has been deposited, the thermal resistance between the sensing element and the sample or reference positions on the substrate whose temperature is being measured is eliminated.

However, a thermal resistance will still exist between the object—the sample or the reference—being measured and the sensor substrate. In the present invention, there is no self-heating error in measuring the temperature of the substrate, regardless of the current applied to the sensor. Thus, within the normal operating temperature range of the sensor, the substrate temperature is measured correctly.

The platinum thin film resistors are applied to ceramic substrates, because ceramic substrates are electrical insulators, can operate at a wide range of temperatures, and are readily adapted to thin film processing. The thermal diffusivity of ceramics varies over a wide range, from the high diffusivity of beryllia ceramic to the low thermal diffusivity of zirconia. By choosing the ceramic substrate, sensors can be made with a very rapid dynamic response (and a lower calorimetric sensitivity) or with a much slower dynamic response (and a greater calorimetric sensitivity) i.e., a rapid dynamic response can be obtained by choosing a substrate with a high thermal diffusivity, or greater thermal diffusivity can be obtained by choosing a substrate with a low calorimetric sensitivity.

It is an object of this invention to provide a differential scanning calorimeter using thin film platinum RTD sensors, which have constant calorimetric sensitivity.

It is a further object of the present invention to provide thin film RTD DSC sensors in which the excitation current is varied in accordance with the temperature of the object (sample or reference) being measured, such that the calorimetric sensitivity of the sensor is constant.

It is a further object of the present invention to provide a differential scanning calorimeter which has a dynamic response which may be high, low or intermediate, depending upon the sensor substrate chosen.

BRIEF DESCRIPTION OF THE FIGURES

FIG. 1a is a cross-section of a portion of the substrate used in the disk-type differential scanning calorimeter of FIG. 1.

DETAILED DESCRIPTION OF THE INVENTION

FIG. 1 is a schematic diagram of a first embodiment of a disk-type RTD differential scanning calorimeter sensor for use in a constant calorimetric sensitivity DSC system of the present invention. FIG. 1 is a bottom view of disk substrate 11. The sample and reference materials are placed on the top surface of substrate. In this first preferred embodiment of the present invention, substrate 11 is a polycrystalline ceramic disk, e.g., alumina, aluminum nitride, beryllia, zirconia or other ceramic disk. Other materials which are electrical insulators, have the desired thermal diffusivity, and are amenable to thin film processing such as monocrystalline ceramics, e.g., sapphire or amorphous materials, i.e., glasses such as quartz glass, may also be used. The specific material for the substrate is selected based upon the desired dynamic thermal response of the calorimeter and any other material characteristics which are desirable, such as corrosion resistance.

Sample platinum resistance temperature sensor 12 and reference platinum resistance temperature sensor 13 are deposited onto the ceramic disk substrate in a serpentine pattern using, e.g., a physical vapor deposition process such as RF sputtering or electron beam evaporation. The serpentine patterns are arranged to cover the portion of the ceramic disk beneath the sample and reference regions. A sensing current is applied to sample RTD 12 via lead wires 14 and 18. Similarly, a sensing current is applied to reference RTD 13 via lead wires 15 and 18. Lead wire 18 is attached to the common termination of the RTDs, and is grounded. Lead wire 14 is attached to the termination of sample RTD 12, and lead wire 15 is attached to the termination of reference RTD 13. Voltage sensing leads 16 and 17 are connected to the terminations of each RTD at the same point as current leads 14 and 15.

The voltage representing the temperature of the sample region of the substrate is measured between lead wires 16 and 18. The voltage representing the temperature of the reference region of the disk is measured between lead wires 17 and 18. The voltage representing the temperature difference between the sample and the reference (and hence the heat flow to the sample) appears between lead wires 16 and 17. Substrate 11 is mounted to the oven of the DSC at the periphery 19 of substrate 11. In the preferred embodiment of the present invention, the RTDs are protected from physical damage by depositing a layer of a dielectric, such as glass or alumina, over the RTDs and a portion of the surrounding substrate. FIG. 1a is a cross-section of a portion of the substrate, showing insulating substrate 11, platinum film 12 (for the sample) or 13 (for the reference), and dielectric layer 20.

Figure 2:
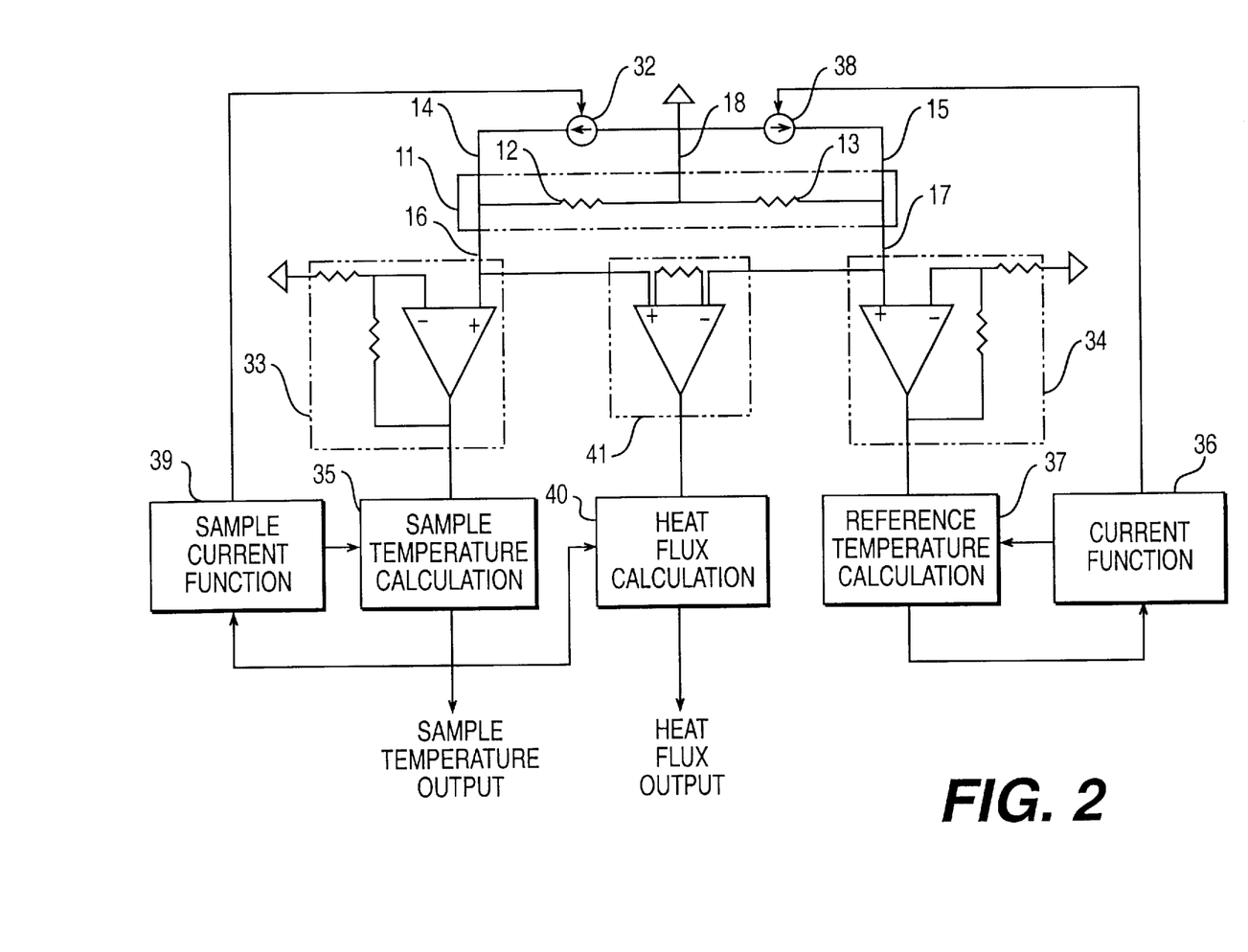
FIG. 2 is a functional block diagram of a constant calorimetric sensitivity differential scanning calorimeter.

FIG. 2 is a functional block diagram which shows how the DSC sensor shown schematically in FIG. 1 is incorporated into the constant calorimetric sensitivity DSC of the present invention. Sample RTD 12 receives a sensing current from controlled current source 32 via lead wires 14 and 18. Similarly, reference RTD 13 receives a sensing current from controlled current source 38 via lead wires 15 and 18. The sample RTD output voltage is supplied to sample temperature amplifier 33 via lead wire 16. The amplified sample voltage is supplied to the sample temperature calculation function 35. Sample temperature calculation function 35 uses the output from sample current function 39 and the amplified sample voltage to calculate the sample RTD resistance. The sample RTD resistance is then used to calculate the sample temperature, using the modified Callender-VanDusen equation:

For T<0° C.: $R_T = R_0[1+AT+BT^2+CT^3(T-100)]$

For T≥0° C.: $R_T = R_0[1+AT+BT^2+CT^3]$ where $R_T$=resistance at temperature T; T is in degrees centigrade; $R_0$ is the resistance at 0° C.; and A, B and C are individually determined for high-precision instruments. Nominal values of the coefficients A, B and C are given in Chapter 3 of HANDBOOK OF APPLIED THERMAL DESIGN, Eric C. Guyer (Editor-in-chief, McGraw-Hill (1989) at page 12–19. The modified Callender-VanDusen equation describes the temperature of a platinum RTD as a function of resistance. The sample temperature is supplied to the sample current function 39, which determines the required current to be supplied to the sample RTD by current source 32 to provide constant calorimetric sensitivity.

The reference RTD output is supplied to reference temperature amplifier 34 via lead wire 17. The amplified reference voltage is supplied to the reference temperature calculation 37, which uses the output from the reference current function 36 and the amplified reference voltage to calculate the reference temperature using the modified Callender-VanDusen equation. The reference temperature is supplied to the reference current function 36, which determines the required current to be supplied to the reference RTD by the current source 38 to achieve constant calorimetric sensitivity.

The sample RTD voltage and the reference RTD voltage are also supplied to amplifier 41. The output of amplifier 41 is proportional to the temperature difference between the sample and reference RTDs, which in turn is proportional to the differential flow of heat to and from the sample with respect to the flow of heat to and from the reference. The output of the differential temperature amplifier and the sample temperature are supplied to the heat flux calculation 40 which calculates the sample heat flow. A calibration routine using standard samples is used to determine the heat flux calculation function. Thus the desired output from the DSC, sample heat flow and sample temperature are obtained.

Calibration of the RTD DSC sensor for operation in a constant calorimetric sensitivity DSC system consists of three separate procedures: 1) correction of inherent imbalances between the sample and reference sides of the sensor; 2) determination of the current versus temperature function that gives constant calorimetric sensitivity; and 3) calibration of the sample heat flow.

Imbalance Correction

When a DSC sensor is manufactured, there will be slight imbalances between the sample and reference sides of the sensor. These differences can be divided into two categories: those due to differences in the RTD sensors themselves, and those which are due to differences in the structure of the support. Although the RTD sensors will be closely matched, small differences in resistance will (in general) still exist. These differences may be dependent upon temperature. During manufacture, the RTDs may be laser-trimmed to correct the resistance to the nominal value, but residual differences will, in general, still exist. The structure which supports the sensors forms the path for heat to flow to and from the sample and reference, resulting in the measured temperature difference. Primarily because of dimensional variations of the structure, the distribution of mass and the thermal resistance of the heat flow paths for the sample and the reference may be slightly different so that the sensor will be unbalanced. The result of these two sources of imbalance taken together may be seen by operating the DSC empty (without any samples, reference materials or pans). This operation should yield no temperature differences, and zero heat flow. All differential scanning calorimeter sensors suffer a combination of these two imbalances to some degree, and correction of the zero heat flow line is necessary.

Calibration of the zero heat flow line for the DSC of the present invention consists of running a heat flow scan, without sample or pans installed in the calorimeter, with a constant excitation current of 1 ma flowing through both sample and reference RTDs. The resulting voltage which appears at the output of the differential amplifier is a measure of the imbalance between the RTDs and the imbalance between sample and reference sides of the structure. To correct the imbalance, the quotient of the output voltage and the RTD resistance is taken, which gives a current. The resulting current, which could be called the unbalance current, is applied to the 1 ma excitation currents by subtracting half of the unbalance current from the 1 ma current for the sample side and adding half of the unbalance current to the 1 ma current for the reference side (note that the sign of the unbalance is included in the calculation). The resultant currents are stored, and are the currents which will correct the DSC zero heat flow line.

Excitation Current Determination

The variable excitation current which will give constant calorimetric sensitivity (volts/watt) is determined by running a 25 mg sapphire sample using the base excitation currents determined in the previous step. The sapphire sample is carefully weighed and loaded in a sample pan. A reference pan is selected that matches the sample pan very closely. A scan is run over the temperature range of interest, and the heat flow voltage signal, sample temperature and heating rate (i.e., the derivative of sample temperature with respect to time) are recorded and stored. The expected heat flow to the sapphire sample is computed as a function of sample temperature, from the sample temperature and the heating rate, using the known heat capacity of sapphire as a function of temperature. The quotient of the output voltage and the computed sample heat flow is calculated. This is the calorimeter heat flow signal, with zero heat flow correction. The calorimeter heat flow signal is then divided by the desired sensitivity, in volts/watt, to give a dimensionless number, which is multiplied by the zero-corrected excitation currents for both the sample and the reference to provide the excitation currents for constant calorimetric sensitivity.

The choice of desired sensitivity is not an arbitrary choice, because increasing the sensitivity will usually result in increased noise levels. Thus, the choice of sensitivity depends upon the level of noise that can be tolerated. Of course, high noise levels ultimately limit the instrument sensitivity, because then weak thermal events cannot be distinguished from the noise. These currents are implemented by the sample current function 39 and the reference current function 36.

Sample Heat Flow Calibration

Heat flow calibration is performed using a sample with a well characterized physical transformation, for example, the melt of a metal such as indium, which occurs in the temperature region of interest for subsequent experiments. A sample is carefully weighed and loaded into a pan and installed in the calorimeter, a closely matched empty pan is installed on the reference position of the calorimeter. A heating scan is run at heating rate equal to the rate that will be used in subsequent experiments. The enthalpy of the transition is measured by integration of the peak area and compared to known values. The ratio of the measured to the standard value is used as a multiplier to scale the output of subsequent experiments.

Calibration of the sample temperature is carried out in the normal fashion, using a series of standards which have well-characterized transitions to correct the sample temperature using a curve fitted to the differences between the measured and correct temperatures for the transitions.

Figure 3:
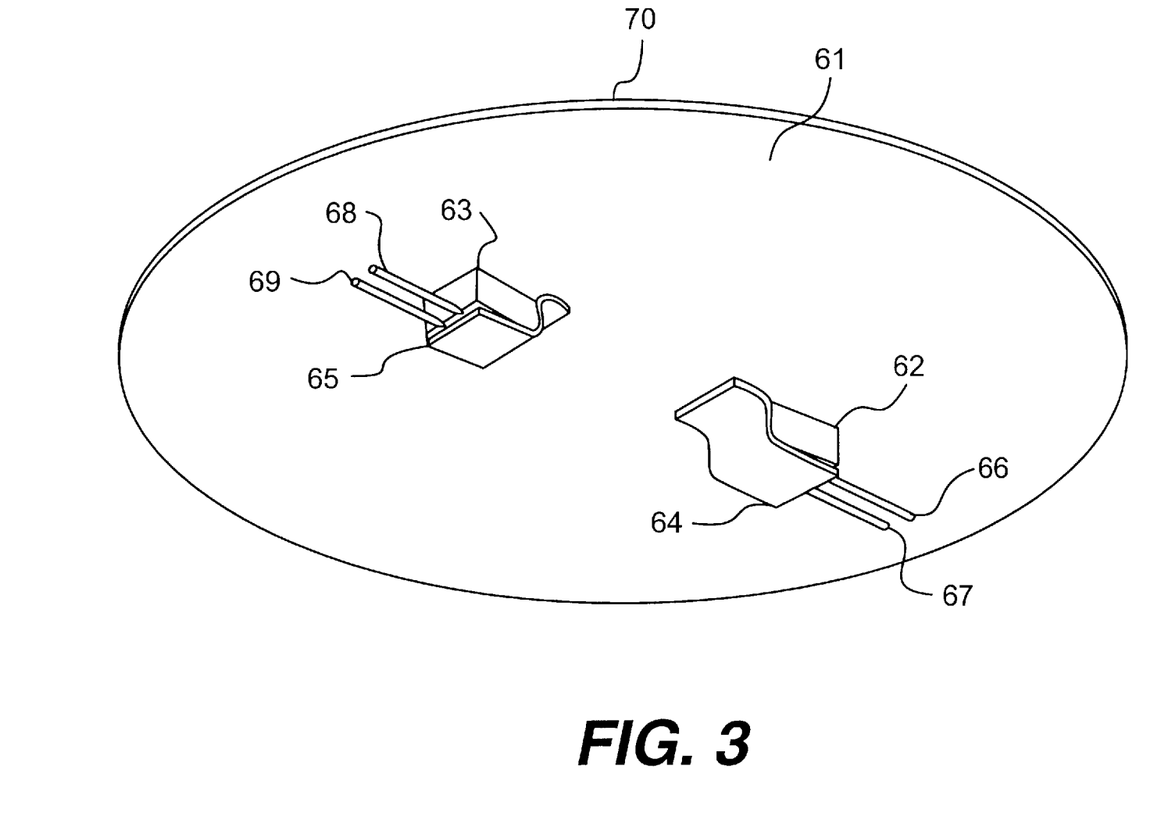
FIG. 3 is a schematic diagram showing the construction of a disk-type differential scanning calorimetry that uses separate RTD sensors mounted to the disk.

A second embodiment of the present invention, using an alternate metallic disk differential scanning calorimeter is shown schematically in FIG. 3. FIG. 3 is a bottom view of the sensor assembly, looking upward at the underside of the metallic disk. The sample and reference pans are placed upon the opposite (top) side of the disk.

Sample RTD 62 is held tightly against metallic disk 61 by clip 64, which is attached to disk 61 in a conventional manner using, e.g., welding. Similarly, reference RTD 63 is held tightly against metallic disk 61 by clip 65 which is similarly attached to disk 61. The RTDs are commercially available thin-film RTDs which have been deposited on an $AL_2O_3$ substrate, e.g., Hy-Cal Model EL-700, available from Hy-Cal Sensing Products, El Monte, Calif. The sample RTD and the reference RTD are in intimate contact with the disk, and are located directly beneath the sample and reference positions. The RTDs thus measure the temperature of the sample and reference regions of the sensor, which are a measure of the sample and reference temperatures, respectively.

The sensor assembly is mounted to the DSC oven at the periphery 70 of metallic disk 61. Lead wires 66 and 68, of the sample and reference RTDs, respectively, each have a pair of extension wires (not shown in FIG. 3) attached. For each RTD, one of the extension wires is used as the current source lead, and the other extension wire is used as the voltage sensing lead. The remaining lead wires, lead wire 67 on the sample RTD and lead wire 69 on the reference RTD also each have a pair of extension wires (not shown) attached. One of the extension wires for each of the RTDs is used connected to ground, and the other is used to measure the voltage appearing across the RTD. The extension wires are connected to the DSC system shown in FIG. 2, similarly to the lead wires of the sensor assembly shown in FIG. 1.

Although the thin film RTD element is not deposited directly on the disk as in the first embodiment, temperature measurement errors due to Joule heating of the RTD are relatively small because the disk to which the RTDs are attached is a relatively good heat conductor. For example, Hy-Cal Model EL-700 thin film RTD, shown on page A10 of the Hy-Cal Summer 1996 catalog, may be used. With a sensing current of 2.3 ma, the temperature rise of the RTD (with respect to the surface temperature) is just 0.02° C. This temperature rise only results in very small errors, which are further minimized when using the temperature calibration procedures described above. Also, the excitation current of 2.3 ma is more than twice as large as the maximum excitation current of 1 ma recommended for this sensor in general purpose applications. The disk in this sensor assembly is metallic, and is a good thermal conductor, as described above.

Figure 4:
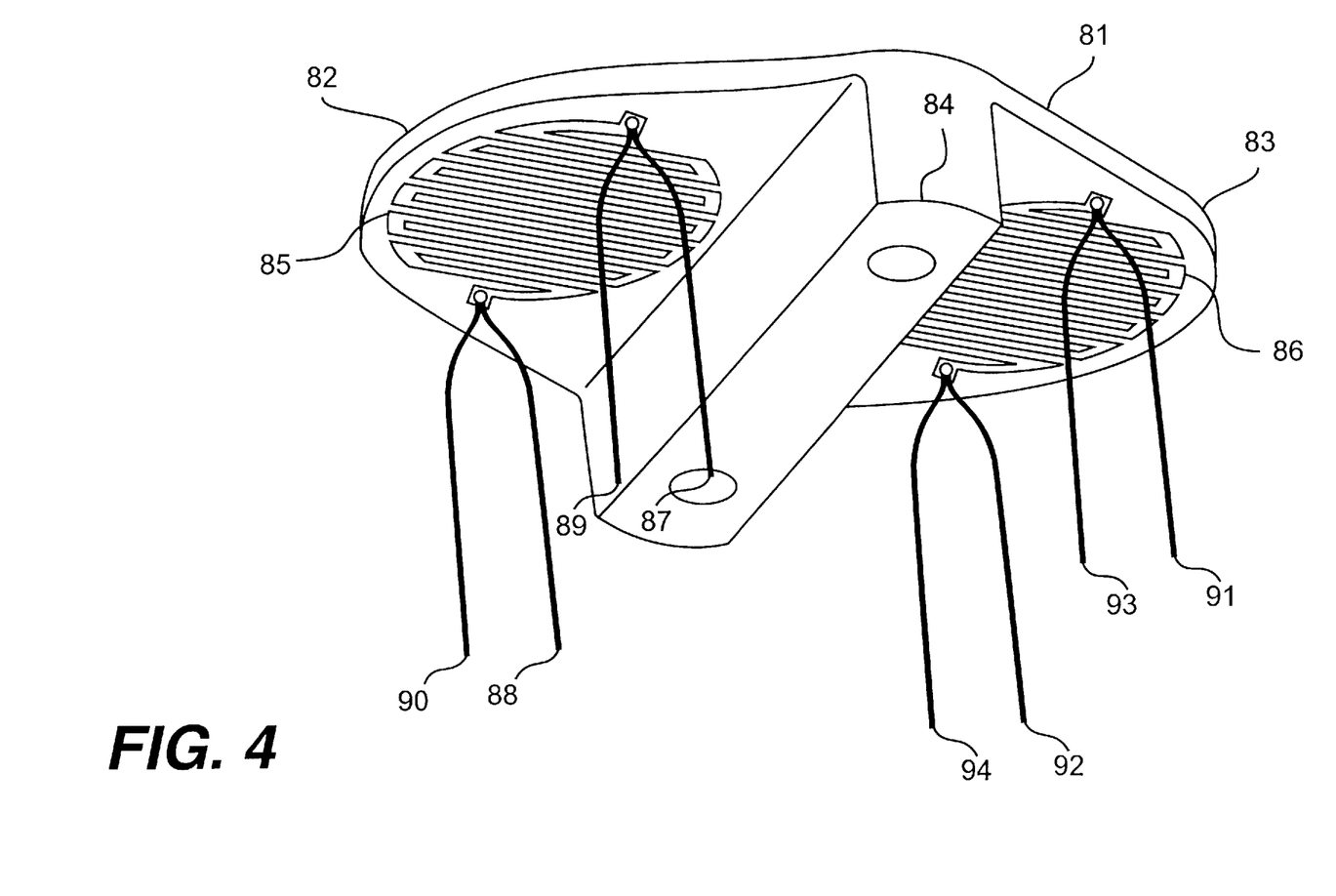
FIG. 4 is a schematic diagram showing the construction of a twin-lug differential scanning calorimeter sensor using RTD temperature sensors for use in a constant calorimetric sensitivity differential scanning calorimeter system.

Another preferred embodiment of a DSC sensor for use in a constant sensitivity DSC is depicted in FIG. 4. The support structure 81 consists of a pair of lugs 82 and 83 and a base 84. The lugs are symmetric with respect to the base structure and form the supports for the sample and the reference. Lug 82 is the sample lug and has a thin film RTD 85 deposited on the same side of the lug as the base. The sample pan (not shown) is placed on the opposite side of the lug from the RTD directly opposite to the RTD. Lug 83 is the reference lug and has a thin film RTD 86 deposited on the same side of the lug as the base. The reference pan (not shown) is placed on the opposite side of the lug from the RTD directly opposite to the RTD.

A pair of lead wires is attached to each end of both RTDs. Lead wire 87 of the sample RTD supplies excitation current to the sample RTD, and lead wire 88 is attached to the ground. Lead wires 89 and 90 are the voltage sensing leads, the voltage representing the RTD resistance (and hence its temperature) is sensed between leads 89 and 90. Lead wire 90 is attached to ground. Lead wire 91 of the reference RTD supplies excitation current to the reference RTD, and lead wire 92 is attached to ground. Lead wires 93 and 94 are the voltage sensing leads. The voltage representing the RTD resistance (and hence its temperature) is sensed between leads 93 and 94. Lead wire 94 is attached to ground.

To apply this sensor in the constant calorimetric sensitivity DSC system described in FIG. 2, lead wire 87 corresponds to lead wire 14 in FIG. 2, 90 corresponds to 16, 91 corresponds to 15, 93 corresponds to 17 and 88, 90, 92 and 94 all correspond to 18.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What we claim is:

1. A sensing system for a differential scanning calorimeter comprising:
    (a) an electrically insulating substrate;
    (b) a sample thin-film resistance temperature detector sensor having a sample output and mounted in a sample region on the electrically insulating substrate;
    (c) a reference thin-film resistance temperature detector sensor having a reference output and mounted in a reference region on the electrically insulating substrate;
    (d) sample current means for providing a sample current to the sample temperature detector sensor for producing a sample output voltage across the sample resistance temperature detector sensor and reference current means for providing a reference current to the reference current detector sensor for producing a reference output voltage across the reference resistance temperature detector sensor;
    (e) a sample temperature amplifier amplifying the sample output voltage and a reference temperature amplifier amplifying the reference output voltage;
    (f) a sample temperature calculation function calculating a temperature for the sample region;
    (g) a reference temperature calculation function calculating a temperature for the reference region;
    (h) means for determining the amplitude of the sample current and means for determining the amplitude of the reference current;
    (i) means for amplifying the difference between the temperature of the sample region and the temperature of the reference region; and
    (j) means for calculating a differential heat flow to the sample with respect to the reference from the amplified difference between the temperature of the sample region and the temperature of the reference region,
    wherein the determined amplitude of the sample current and the determined amplitude of the reference current are modified so as to obtain an amplitude for said currents such that the calorimeter has constant calorimetric sensitivity over a desired temperature range.

2. The sensing system of claim 1, wherein the temperature of the sample region and the temperature of the reference region are determined using the modified Callender-VanDusen equation.

3. The sensing system of claim 1, further comprising a sample pan placed on the side of the substrate opposite to the side on which the sample resistance temperature detector is mounted, and a reference pan placed on the side of the substrate opposite to the side on which the reference resistance temperature detector is mounted.

4. The sensing system of claim 1, wherein the reference thin-film sample temperature detector is a platinum thin film resistor, and wherein the reference thin-film resistance temperature detector is also a platinum thin film resistor.

5. The sensing system of claim 4, wherein the platinum thin films are deposited on the insulating substrate.

6. The sensing system of claim 4, further comprising a layer of dielectric material over the sample resistance temperature detector sensor and a layer of dielectric material over the reference resistance temperature detector sensor.

7. The sensing system of claim 1, wherein the electrically insulating substrate comprises a symmetric pair of lugs and a base.

8. The sensing system of claim 1, wherein the electrically insulating substrate is a polycrystalline ceramic disk.

9. The sensing system of claim 1, wherein the electrically insulating substrate is a disk fabricated from an amorphous material.

10. A method for measuring the differential heat flow to a sample with respect to a reference comprising:
    (a) providing a sample thin-film resistance temperature detector sensor deposited on a sample region on a first surface of an electrically insulating substrate and a reference thin-film resistance temperature detector sensor deposited on a reference region on the first surface of the electrically insulating substrate;
    (b) placing a sample in a sample pan and a reference pan on a surface of the electrically insulating substrate opposite to the first surface of the electrically insulating substrate;
    (c) providing a sample sensing current to the sample thin-film resistance temperature detector, said sample sensing current producing a sample output voltage across the sample resistance detector, and providing a reference sensing current to the reference thin-film temperature detector, said reference sensing current producing a reference output voltage across the reference resistance detector;
    (d) measuring the amplitude of the sample output voltage and measuring the amplitude of the reference output voltage;
    (e) determining the amplitude of the sample sensing current and the amplitude of the reference sensing current, and modifying the determined amplitudes of said sample and reference sensing currents so as to obtain amplitudes for said sensing currents such that the calorimeter provides constant calorimetric sensitivity over a desired temperature range;
    (f) calculating the temperature of the sample region and the temperature of the reference region from the amplitude of the sample output voltage and the amplitude of the reference output voltage;
    (g) amplifying the difference between the temperature of the sample region and the temperature of the reference region; and
    (h) calculating a differential heat flow to the sample with respect to the reference from the amplified difference between the temperature of the sample region and the temperature of the reference region.

11. The method of claim 10, further comprising calibrating a zero differential heat flow line, said zero differential heat flow calibration comprising running a heat flow scan prior to placing the sample pan and the reference on the surface of the electrically insulating substrate.

12. The method of claim 10, further comprising calculating a sample base excitation current and a reference base excitation current.

13. The method of claim 12 further comprising determining the excitation currents which will provide constant calorimetric sensitivity by running a scan of a sapphire reference over the temperature range of interest using the sample base excitation current and the reference base excitation current.

14. The method of claim 13, comprising computing the heat flow to the sapphire sample as a function of sample temperature using the known heat capacity of sapphire.

15. The method of claim 14, comprising calculating the quotient of the sample output voltage to the computed heat flow to the sapphire sample.

16. The method of claim 15, comprising obtaining the excitation currents required for constant calorimetric sensitivity by dividing the quotient of the sample output voltage to the computed heat flow to the sapphire sample by the desired calorimetric sensitivity.

17. A differential scanning calorimeter comprising:
(a) an electrically insulating ceramic substrate having a top surface and a bottom surface;
(b) a sample thin-film resistance temperature detector sensor deposited on the bottom surface of the electrically insulating ceramic substrate;
(c) a reference thin-film resistance temperature detector sensor deposited on the bottom surface of the electrically insulating ceramic substrate;
(d) a protective layer of dielectric covering the sample thin-film resistance temperature detector sensor and a protective layer of dielectric covering the reference thin-film resistance temperature detector sensor;
(e) a sample in a sample pan placed on the top surface of the ceramic substrate opposite to the sample thin-film resistance temperature detector sensor, and a reference pan placed on the top surface of the ceramic substrate opposite to the reference thin-film resistance temperature detector sensor;
(f) means for applying a sample sensing current to the sample thin-film resistance temperature detector and means for applying a reference sensing current to the reference thin film temperature detector;
(g) means for measuring a sample output voltage across the sample thin-film resistance temperature detector sensor and means for measuring a reference output voltage across the reference thin-film resistance temperature detector sensor; and
(h) means for calculating the temperature of the sample pan from the sample output voltage, and means for calculating the temperature of the reference pan from the reference output voltage;
(i) means for determining and amplifying the difference between the temperature of the sample pan and the temperature of the reference pan; and
(j) means for calculating the differential heat flow to the sample from the amplified difference between the temperature of the sample pan and the temperature of the reference pan,
wherein the amplitudes of the sample sensing current and the reference sensing current are determined and modified so as to obtain amplitudes for said sensing currents so as to provide constant calorimetric sensitivity for the calorimeter over a desired temperature range.

18. The differential scanning calorimeter of claim 17, wherein the ceramic substrate has a high thermal diffusivity such that the differential scanning calorimeter has a relatively rapid dynamic response.

19. The differential scanning calorimeter of claim 17, wherein the ceramic substrate has a low thermal diffusivity such that the differential scanning calorimeter has a relatively greater calorimetric sensitivity.

20. The differential scanning calorimeter of claim 17, wherein the sample and reference thin film temperature resistance detectors are deposited on the ceramic substrate in a serpentine pattern.

21. The differential scanning calorimeter of claim 17, wherein the ceramic substrate comprises a base portion, a sample lug portion and a reference lug portion, and wherein the sample lug and the reference lug are symmetrically and planarly disposed on either side of the base.

22. The differential scanning calorimeter of claim 17, wherein the ceramic substrate is selected from alumina, aluminum nitride, beryllia and zirconia.

23. A sensing system for a differential scanning calorimeter comprising:
(a) a metallic disk;
(b) a sample thin-film resistance temperature detector sensor mounted in a sample region of the metallic disk;
(c) a reference thin-film resistance temperature detector sensor mounted in a reference region of the metallic disk;
(d) sample current means for producing a sample sensing current for the sample sensor and reference current means for producing a sensing current for the reference sensor, said sample current means producing a sample output voltage and said reference current means producing a reference output voltage;
(e) a sample temperature amplifier amplifying the sample output voltage and a reference temperature amplifier amplifying the reference output voltage;
(f) a sample temperature calculation function calculating a temperature for the sample region:
(g) a reference temperature calculation function calculating a temperature for the reference region;
(h) means for determining the amplitude of the sample sensing current and the amplitude of the reference sensing current and for modifying the determined amplitudes of said sensing currents so as to obtain amplitudes for said sensing currents such that the calorimeter provides constant calorimetric sensitivity over a desired temperature range;
(i) means for determining and amplifying the difference between the temperature of the sample region and the temperature of the reference region; and
(j) means for calculating the amplitude of the differential heat flow to the sample with respect to the reference from the amplified difference between the temperature of the sample region and the temperature of the reference region.

24. The sensing system of claim 23, wherein the temperature of the sample region and the temperature of the reference region are determined using the modified Callender-VanDusen equation.

25. The sensing system of claim 23, further comprising a sample pan placed on the side of the metallic disk opposite to the side on which the sample resistance temperature detector is mounted, and a reference pan placed on the side of the metallic disk opposite to the side on which the reference resistance temperature detector is mounted.

26. The sensing system of claim 23, wherein the thin film resistance temperature detectors are held against the metallic disk by a clip.

\* \* \* \* \*